US012728251B2

(12) United States Patent
Chelli et al.

(10) Patent No.: US 12,728,251 B2
(45) Date of Patent: Sep. 8, 2026

(54) CONNECTOR SYSTEM

(71) Applicant: Bellco S.R.L., Mirandola (IT)

(72) Inventors: Niccolo Chelli, Rufina (IT); Angela Visciano, Modena (IT)

(73) Assignee: Bellco S.R.L., Mirandola (IT)

( * ) Notice: Subject to any disclaimer, the term of this patent is extended or adjusted under 35 U.S.C. 154(b) by 1031 days.

(21) Appl. No.: 17/198,943

(22) Filed: Mar. 11, 2021

(65) Prior Publication Data

US 2022/0288374 A1 Sep. 15, 2022

(51) Int. Cl.
*A61M 39/10* (2006.01)
*A61M 1/14* (2006.01)

(52) U.S. Cl.
CPC .............. *A61M 39/10* (2013.01); *A61M 1/14* (2013.01); *A61M 2039/1072* (2013.01); *A61M 2205/0216* (2013.01); *A61M 2205/0266* (2013.01)

(58) Field of Classification Search
None
See application file for complete search history.

(56) References Cited

U.S. PATENT DOCUMENTS 4,294,250 A * 10/1981 Dennehey ............. A61M 39/10 604/905
6,234,538 B1 5/2001 Lauer
10,821,239 B2 11/2020 Hanson et al.
2003/0208165 A1* 11/2003 Christensen .......... A61M 39/26 264/494
2004/0073176 A1* 4/2004 Utterberg .............. A61M 39/26 604/256
2005/0171489 A1* 8/2005 Weaver ................. A61M 39/24 604/247
2007/0007208 A1* 1/2007 Brugger ................ A61M 1/288 210/645

(Continued)

FOREIGN PATENT DOCUMENTS

CN 104470566 A 3/2015
CN 104640597 A 5/2015

(Continued)

OTHER PUBLICATIONS

Response to Communication Pursuant to Rules 161(1) and 162 EPC dated Oct. 19, 2023, from counterpart European Application No. 22710741.4, filed Apr. 19, 2024, 16 pp.

(Continued)

*Primary Examiner* — Jonathan M Peo

(57) ABSTRACT

A connector includes a plug and a socket. The plug defines a channel extending between a plug inlet defined by the plug and a plug outlet defined by the plug, where the plug inlet is configured to mechanically and fluidically engage a first conduit. The socket includes a socket body defining a socket well and a socket membrane. The socket is configured to mechanically and fluidically engage a second conduit, and the plug is configured to insert into the socket well to mechanically mate with the socket. The socket membrane is positioned within the socket well and is biased to a closed position in which the socket membrane blocks fluid flow through the socket well. When the plug is inserted into the socket well, the socket membrane is configured to open to enable fluid flow through the socket well.

21 Claims, 5 Drawing Sheets

(56) References Cited

U.S. PATENT DOCUMENTS

| | | | | |
|---|---|---|---|---|
| 2007/0225635 | A1* | 9/2007 | Lynn | A61M 39/20 604/30 |
| 2009/0120864 | A1* | 5/2009 | Fulkerson | A61M 1/16 210/321.71 |
| 2015/0119863 | A1* | 4/2015 | Christensen | A61M 39/10 604/539 |
| 2015/0190627 | A1 | 7/2015 | Ueda et al. | |
| 2017/0281847 | A1 | 10/2017 | Manda et al. | |

FOREIGN PATENT DOCUMENTS

| | | | |
|---|---|---|---|
| CN | 107308513 | A | 11/2017 |
| EP | 0575970 | B1 | 9/1999 |

OTHER PUBLICATIONS

International Search Report and Written Opinion of International Application No. PCT/IB2022/052054 dated Jul. 19, 2022, 15 pp.

First Office Action and Search Report, and translation thereof, from counterpart Chinese Application No. 202280027817.0 dated Mar. 25, 2026, 10 pp.

* cited by examiner 136C
136B
124
T
134
C1
C2
136A 137C
124
136B
136C
136A
137B
137A

CONNECTOR SYSTEM

TECHNICAL FIELD

This disclosure is related to a fluid system connector.

BACKGROUND

Dialysis machines may be used to remove waste products from blood of a patient when the kidneys of the patient are no longer able to adequately do so. During dialysis, the dialysis machine may generate or regenerate dialysate using specified concentrations of solute buffers, osmotic agents, cations, and/or other concentrates for biocompatibility with the patient. The dialysis machine may provide the dialysate to a cycler for delivery to the patient. The generation or regeneration of dialysate may require a patient or another user to perform physical connections between disposable elements and the dialysis machine.

SUMMARY

This disclosure describes a connector configured to establish a connection between a container configured to store a material, such as a medical solution in fluid form, solid form, or any other suitable form, and a machine line of a medical machine (e.g., a dialysis machine) configured to utilize the material to provide therapy to a patient. The connector is configured to establish the connection through the mechanical mating of a plug and a socket. The plug is configured to fluidically engage the container and the socket is configured to fluidically engage the machine line. In some examples, the plug is configured to insert into a socket well defined by the socket to provide the mechanical mating. The socket includes a socket membrane positioned within the socket well that is biased to a closed position in which the socket membrane blocks entry into the socket well and into the machine line. When the plug is inserted into the socket well, the plug moves the socket membrane to open the membrane and enable fluid flow through the socket well and into the machine line.

In some examples, a connector comprises a plug defining a channel extending between a plug inlet defined by the plug and a plug outlet defined by the plug, wherein the plug inlet is configured to mechanically and fluidically engage a first conduit; a socket includes a socket body defining a socket well, wherein the socket is configured to mechanically and fluidically engage a second conduit, and wherein the plug is configured to insert into the socket well to mechanically mate with the socket; and a socket membrane biased to a closed position in which the socket membrane blocks fluid flow through the socket well, and wherein, when the plug is inserted into the socket well, the socket membrane is configured to open to enable fluid flow through the socket well. In some examples, the socket membrane may be positioned within the socket well or connected to a dialysis machine housing.

The details of one or more examples are set forth in the accompanying drawings and the description below. Other features, objects, and advantages will be apparent from the description and drawings, and from the claims.

DETAILED DESCRIPTION

Figure 1:
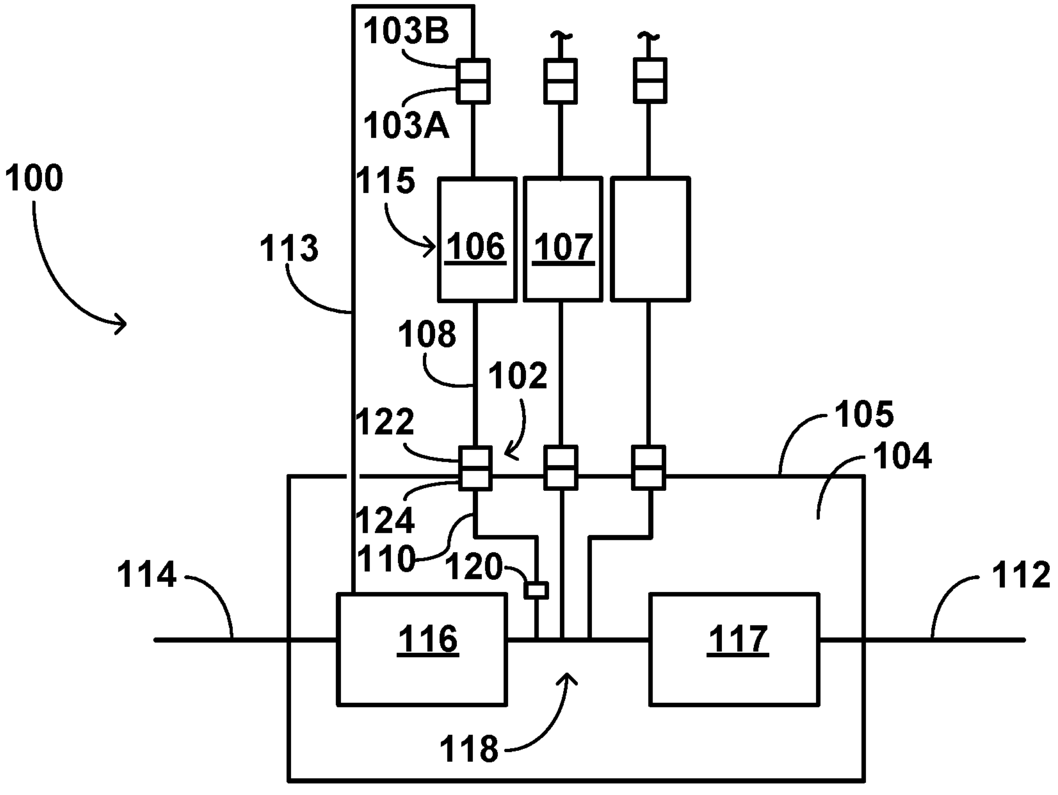
FIG. 1 is a conceptual diagram illustrating an example medical system configured to deliver a medical fluid such as dialysate.

This disclosure describes a connector configured to establish a fluid connection between a medical machine and a container that stores material for use by the medical machine in a medical treatment of a patient. In some examples, the connector is configured to provide a fluid connection between a materials source, such as a medical solution container (e.g., a bag) holding a medical solution (e.g., in a solid and/or a liquid state), and a medical machine configured to utilize the medical solution to provide therapy to a patient. In some examples, the container stores a concentrate solution for dialysis therapy and the medical machine includes a dialysis machine configured to utilize the concentrate solution to deliver dialysate to the patient.

The connector includes a plug configured to mechanically mate with a socket to provide the connection. For example, the connector may be configured such that the plug inserts into a socket well defined by the socket (e.g., by the patient, a patient caretaker, a clinician, or another user) to mechanically mate with the socket. The socket includes a socket membrane positioned within the socket well. The socket membrane is configured to act as a valve in that the socket membrane may block or allow passage of material into and out of the socket well. The socket membrane may be biased to a closed position in which the socket membrane blocks fluid flow through the socket well. When the plug is inserted into the socket well, the positive pressure applied by the plug opens the socket membrane to enable fluid flow through the socket well. For example, the plug may push the socket membrane towards an inner surface of the socket defining the socket well as the plug inserts into the socket well, thereby opening a fluid channel through the socket well.

The connector may be configured to help preserve the sterility of medical systems involving pharmacological preparation and delivery to a patient. For example, the connector may be advantageous when a procedure requires the patient or another user (e.g., patient caretaker or clinician) to make a physical connection between a container, such as a disposable concentrate bag, and a medical machine, such as a dialysis machine. The socket membrane of the connector may be used to physically separate a hydraulic circuit of a medical machine from the external environment, thereby reducing the possibility of contaminants entering the hydraulic circuit and/or facilitating a disinfection process of the medical machine. For example, the socket may be fluidically connected to a fluid conduit of the medical machine and the socket membrane may substantially seal (e.g., fully seal or nearly fully seal to the extent permitted by the material and configuration of the membrane) the fluid pathway from the external environment into the fluid conduit of the medical machine while a plug is not inserted into the socket. The integration of the socket membrane into the socket may make it unnecessary to reposition the socket membrane after removal of the plug, thereby helping to block the entry of contaminants into the medical machine while minimizing user efforts needed to block the fluid pathway into the medical machine.

The plug of the connector is configured to mechanically and fluidically engage a first conduit such as a container tube connected to a medical solution container. The plug is configured to mechanically and fluidically engage the first conduit to fluidly couple the first conduit and a plug inlet defined by the plug. The plug defines a channel ("plug channel") extending from the plug inlet to a plug outlet defined by the plug. The plug is configured such that, when the plug mechanically and fluidically engages the first conduit, the plug establishes a flow path (e.g., for a therapeutic agent or component for the therapeutic agent) from a lumen of the first conduit, through the plug channel, and to the plug outlet. The first conduit and plug channel may each be configured to establish a flow path for material in fluid or solid form.

The socket of the connector is configured to mechanically and fluidically engage a second conduit, such as a hydraulic line within a medical machine ("machine line"). The socket is configured to mechanically and fluidically engage the second conduit to fluidly couple the plug outlet and the second conduit. The socket is configured such that, when the plug mechanically mates with the socket, the connector establishes a flow path from a lumen of the first conduit mechanically and fluidically engaged by the plug to a lumen of the second conduit mechanically and fluidically engaged by the socket. The plug is configured to insert into a socket well defined by the socket to mechanically mate with the socket. For example, the plug may have an interference fit with the socket well directly or with the socket membrane to provide a fluid seal between the plug and the socket well that prevents fluid from entering and/or exiting at the connection established by the connector. This may enable an O-ring or other separate fluid seal to be eliminated from the socket and plug connection. As another example, the plug and socket may define interlocking structures to mechanically connect together and align the respective plug channel and the socket well.

In some examples, a housing of a medical machine (e.g., a dialysis machine) mechanically supports the socket and the machine line. For example, the socket may be affixed to or be an integral part of the housing, and the machine line may be affixed to or be an integral part of the socket and/or housing. Hence, the connector may be configured such that a user (e.g., a patient, patient caretaker, or clinician) may translate the plug toward the socket to mechanically mate the plug and socket and fluidly couple a first conduit (e.g., tubing for a container) and a second conduit (e.g., a machine line within a medical machine), enabling the medical machine to utilize a material within the container, e.g., to prepare a medication before delivering it to the patient and to provide therapy to the patient. The second conduit may be configured to establish a flow path for material in fluid or solid form.

The connector includes a socket membrane positioned within the socket well and configured to act as a valve. The socket membrane is biased to a closed position in which the socket membrane substantially blocks (e.g., fully blocks or blocks most of the socket well) the flow of material (e.g., air, dialysate, environmental contaminants, disinfection fluid, and the like) through the socket well. For example, the socket membrane may block the socket well to prevent disinfection fluid from flowing outside the hydraulic circuit of the medical system during disinfection. The socket membrane is configured to be opened by the plug being inserted into the socket well to enable fluid flow through the socket well. In some examples, the socket membrane is deformable and configured to position between an outer surface of the plug and an inner surface of the socket well in response to insertion of the plug into the socket well. In this way, the socket membrane may open the socket well and enable fluid flow through the socket well past the location of the socket membrane, e.g., from a location proximal to the socket membrane to a location distal to the socket membrane.

In examples, the socket membrane includes a plurality of leaflets (e.g., two, three, four, five, six, or more) configured to coapt to define the closed position. That is, the leaflets may work together to close the fluid path through the socket well when the leaflets are biased to the closed position (e.g., similar to leaflets of a native heart valve). The leaflets define free edges configured to move distally away from the plug when the plug is inserted into the socket well. Responsive to removal of the plug from the socket well, the leaflets may return to the closed position, thereby closing the socket well and blocking the entry of contaminants into the hydraulic circuit. This may help maintain the sterility of the hydraulic circuit of the medical machine.

The socket includes a socket body defining a socket well configured to receive some portion of a body of a plug ("plug body"). The plug may be configured to substantially insert into the socket well to mechanically mate the plug and the socket. The socket may be configured to fluidly couple the plug inlet and the machine line when the plug mechanically mates with the socket and the socket mechanically and fluidically engages the machine line.

In some examples, the plug includes a rim configured to contact the socket body to control a depth of insertion of the plug into the socket well. For example, the rim may extend from the outer surface of the plug. The rim may be used to facilitate physical mating between the plug and the socket and improve usability of the plug. For example, a user may engage the rim and/or a region proximal to the rim to grip, push, and/or the like the plug when applying force to insert the plug into the socket well. The rim can, for example, serve as a support for a thumb and an index finger of the user or the user can direct grip the rim. Additionally, in some examples, the socket body may include a flange configured to contact the rim when the plug is fully inserted in the socket well, in this way indicating to a user that a proper connection has been established.

In some examples, the connector is configured to assist in the proper fluid connection between a container and a particular fluid conduit of a medical machine. This may increase the success of at-home therapies (e.g., dialysis) that require a patient or other user to make fluid connections between a material source and a medical machine by at least helping the patient (or other user) fluidically connect a material source to the correct fluid line of the medical machine.

For example, the connector may include one or more visible indications that helps the user properly align a particular container with the correct fluid conduit of the medical machine. As an example, a plug attached to a particular container may have a color and/or include a marking (e.g., a graphical marking, an alphanumeric marking, and/or the like) corresponding to a color and/or marking of a specific socket of a medical machine. The specific socket of the connector may be configured to provide the contents of the particular container to the medical machine, such that the medical machine generates a therapeutic agent using the contents of the particular container. Substantially matching the corresponding color and/or markings of the plug and the socket may assist the patient or other user in the proper placement of the plug in the correct socket.

In addition to, or instead of, the visible indications, a particular plug may be configured to mate with a respective socket and to not mate with other sockets of the medical machine to help a user better determine which socket a particular plug should be inserted into in order to properly connect a container fluidically connected to the plug with the medical machine. For example, the plug and socket may have corresponding dimensions and/or shapes that indicate to a user that a certain plug is configured to fit within a particular socket of the medical machine.

FIG. 1 is a block diagram illustrating an example medical system 100 using an example connector 102. Medical system 100 includes a medical machine 104 configured to produce a medical solution for a patient therapy (e.g., dialysis) using one or more concentrate solutions and/or reconstituted solutions. For example, medical machine 104 may be configured to produce dialysate for the patient using concentrates contained in one or more containers, such as container 106, container 107, and/or the like. The concentrates can be, for example, concentrate solutions, which may need to be diluted prior to use, or powdered concentrates that are reconstituted prior to use. Medical system 100 may be configured to generate the medical solution by at least mixing a concentrate within container 106 with a fluid such as water. In some examples, medical system 100 is configured to receive the fluid via fluid line 114 and deliver the medical solution produced (e.g., dialysate) via an infusion line 112. For example, infusion line 112 may provide dialysate (or a component thereof) to a dialysis cycler configured to provide therapy to a patient using the dialysate, or to a container configured to retain the dialysate for subsequent use.

In some examples, medical system 100 includes a conditioning system 116 configured to provide fluid received via infusion line 112 to a flow path 118 defined by medical machine 104. Conditioning system 116 may include, for example, a pump configured to provide a motive force to the fluid received via infusion line 112 to drive the fluid through flow path 118. In some examples, conditioning system 116 may include one or more filters and/or sorbent cartridges configured to remove impurities (e.g., particulate matter and/or ions) from the fluid prior to the fluid entering flow path 118. In addition, in some examples, conditioning system 116 may include one or more sensors, such as a conductivity sensor and/or a pressure sensor, configured to monitor a physical state or condition of the fluid prior to the fluid entering flow path 118. In examples, conditioning system 116 includes a degasser configured to degas the fluid prior to entering flow path 118. The degasser may include, for example, a vacuum pump configured to create a vacuum to remove air and other gases from the fluid prior to entering flow path 118.

Medical system 100 may be configured to generate a medication using the one or more concentrates held in one or more containers such as container 106 and container 107. One or more of the containers can be connected to medical machine 104 using connectors 102 described herein. Thus, although only one connector 102 is labeled in FIG. 1, in other examples, container 107 and other containers of system 100 can be fluidically connected to medical machine 104 with similar connectors 102, and the description of container 106 may also apply to container 107 and other containers of system 100.

In examples, medical system 100 may be configured to provide a fluid (e.g., purified water) to a container system 115 including container 106 such that container system 115 may generate the medical solution. For example, medical system 100 may be configured to receive a fluid via fluid line 114 and provide the fluid (e.g., from conditioning system 116) to container system 115 using a machine fluid line 113. In some examples, container system 115 may be configured to utilize a single fluid path for both an injection of fluid (e.g., purified water) into container system 115 and extraction of a medical solution. For example, container system 115 may be configured to receive the fluid via second conduit 110 and first conduit 108 in a first flow direction to generate a medical solution, and then supply the medical solution via second conduit 110 and first conduit 108 in a second flow direction opposite the first flow direction.

In examples, medical system 100 includes one or more concentrate pumps such as concentrate pump 120 configured to inject a concentrate from container 106 into flow path 118 via second conduit 110. In some examples, medical system 100 may include one or more additional filters (not shown) configured to filter the concentrate provided from container 106 prior to the concentrate entering flow path 118. The concentrate may include one or more solutes. In examples, the solute includes an osmotic agent such as glucose, dextrin, and/or icodextrin. In examples, the solute includes an ion such as sodium chloride, sodium lactate, magnesium chloride, calcium chloride, potassium chloride, and/or sodium bicarbonate.

Connector 102 is configured to fluidly couple first conduit 108 and second conduit 110, to enable medical system 100 to introduce a concentrate held within container 106 into flow path 118. Connector 102 includes a plug 122 mechanically and fluidically engaged with first conduit 108 and a socket 124 mechanically and fluidically engaged with second conduit 110. Plug 122 is configured to mechanically mate with socket 124 such that a confined fluid path is established from an interior of container 106, through first conduit 108, and to second conduit 110. In examples, connector 102 defines the confined fluid path through a plug channel (FIG. 2) defined by a body of plug 122. The plug channel may extend from a plug inlet (FIG. 2) defined by plug 122 to a plug outlet (FIG. 2) defined by plug 122. The plug inlet may be configured to mechanically and fluidically engage first conduit 108 such that first conduit 108 is fluidically coupled with the plug inlet.

In some examples, plug 122 is a disposable plug configured to be disposed of when one or more components of container system 115 are replaced. In addition, in some examples, plug 122 is provided separate from first conduit 108 or is preattached to first conduit 108 and configured to be delivered to medical system 100 as part of container system 115. Plug 122 may be formed using one or more of polymer, metal, or any other suitable material or combination of materials.

Plug 122 is configured to mechanically mate with socket 124 such that the plug outlet is fluidically coupled to second conduit 110 when second conduit 110 is mechanically and fluidically engaged by socket 124. In examples, socket 124 defines a socket well, and plug 122 is configured to insert into the socket well to mechanically mate with socket 124. For example, plug 122 can have a hollow cylindrical body configured to be received in a cylindrical socket well. Other shapes of plugs and socket wells may also be used in other examples. In some examples, socket 124 is mechanically supported by a housing 105 of medical machine 104. Hence, connector 102 may be configured to define a confined fluid path from an interior of container 106 to flow path 118.

Connector 102 is configured to help prevent the introduction of contaminants into medical machine 104 when, for example, plug 122 is not positioned in socket 124. As discussed in further detail below (e.g., with respect to FIGS. 2 and 3), socket 124 includes a socket membrane positioned within the socket well. The socket membrane is biased to a closed position in which the socket membrane substantially blocks ingress (and, in some examples, egress) of materials through socket well 134. That is, the socket membrane is configured to fully block or nearly fully block socket well 134. This may prevent passage of containments through socket well 134 into second conduit 110 and escape of disinfection fluid through socket well 134 out of the hydraulic circuit of medical system 100. In some examples, the socket membrane may block at least 90% of the area of the socket well, such as at least 90%-100%, or 90% to 95%.

The socket membrane may include a plurality of leaflets that are configured to coapt to define the closed position. Consequently, prior to physically mating plug 122 and socket 124 and when nothing is in socket well 134 applying a positive pressure pushing the socket membrane open, the socket membrane is in a closed position that minimizes or even prevents the ingress of contaminants from entering or exiting second conduit 110, thereby reducing the risk of contamination of second conduit 110. When plug 122 is inserted into the socket well, the plug opens the socket membrane to enable fluid flow through the socket well. For example, the leaflets of the socket membrane may define free edges configured to move distally away from plug 122 when plug 122 is inserted through the socket membrane and into the socket well. That is, plug 122 may push the leaflets out of the way and open a fluid pathway through the socket well. Responsive to removal of plug 122 from the socket well, the leaflets or other socket membrane configuration may return to the closed position due to their bias to the closed position.

In some examples, medical machine 104 may be configured to receive the particular contents of container 106 within second conduit 110. In some examples, connector 102 is configured to help facilitate the proper connection between container 106 and a specific socket 124. For example, connector 102 can include one or more visible indications to assist in the proper connection of specific plugs with specific sockets, such as the connection of plug 122 and socket 124.

For example, plug 122 may be a component of container system 115 including container 106, first conduit 108, and plug 122. First conduit 108 may be a flexible tube (e.g., disposable or reusable) fluidly connected to an interior of container 106. Medical machine 104 may be configured to receive the particular contents of container 106 via socket 124, in order to produce a particular medical solution for the treatment of a patient. Plug 122 may include a visual indicia (e.g., a color and/or include a marking) corresponding to a visual indicia of socket 124 of medical machine 104 to assist the patient or other user in the proper placement of a specific plug such as plug 122 in a specific socket such as socket 124. In addition to or instead of the visual indicia, plug 122 and socket 124 may be sized to fit together and other plugs and sockets of system 100 may have different sizes so as to provide an indication to the user that plug 122 and socket 124 are intended to fit together. The size can be, for example, a cross-sectional dimension (e.g., a diameter), a depth of insertion of plug 122 into socket 124, or the like or combination thereof.

Container system 115 may further include a first fluid connector 103A configured to fluidly couple container 106 and machine fluid line 113. In examples, first fluid connector 103 is configured to mechanically mate with a second fluid connector 103B of machine fluid line 113 to provide the fluid coupling. In some examples, as discussed above, container system 115 may be configured to utilize a single fluid path for both an injection of fluid and extraction of medical solution. Hence, container system 115 may be a separable system configured to attach to and/or detach from medical machine 104. First fluid connector 103A and/or socket 124 may be configured such that a patient or care-giver may connect container system 115 to medical machine 104 in preparation for use of a medical solution provided by container system 115.

Medical system 100 may further include a mixing system 117 configured to provide the medical solution to infusion line 112. In examples, mixing system 117 includes a mixing chamber configured to further mix the concentrate from container 106 and the fluid from conditioning system 116. Mixing system 117 may include one or more sensors configured to evaluate one or more characteristics of the medical solution, such as one or more of conductivity sensors, pH sensors, pressure sensors, flow sensors, or the like. In some examples, mixing system 117 includes one or more sterilization units, such as one or more ultrafilters, microbial filters, UV light sources, or other sterilization units configured to substantially sterilize dialysate prior to infusion into a patient.

Hence, connector 102 may be configured to fluidly couple first conduit 108 and second conduit 110, such that medical system 100 may produce a medical solution (e.g., dialysate) using one or more concentrates delivered via first conduit 108. Connector 102 may provide the fluidic coupling using plug 122 configured to mechanically mate with socket 124. Socket 124 may be configured to fluidly couple the plug inlet and second conduit 110 when plug 122 mechanically mates with socket 124 and socket 124 mechanically and fluidically engages second conduit 110. Prior to establishing the physical connection between plug 122 and socket 124, the socket membrane positioned in the socket well may be in a closed position, forming a seal minimizing or even preventing contaminants from entering or exiting second conduit 110. Responsive to insertion of plug 122 into socket 124, the socket membrane opens to enable fluid flow through the socket well to establish a confined fluid path extending from the interior of container 106, through connector 102, and to flow path 118.

Figure 2:
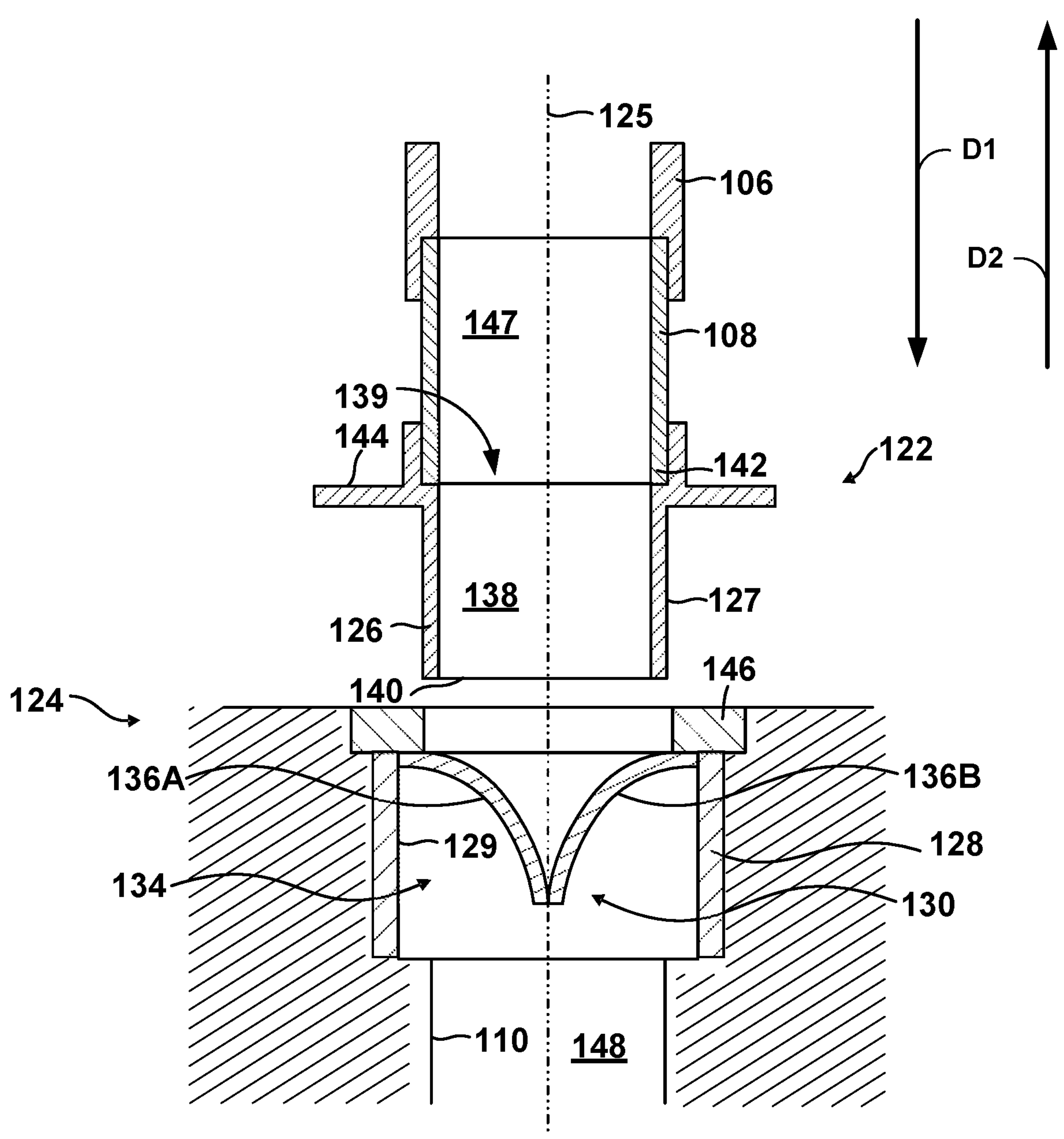
FIG. 2 is a conceptual cross-sectional diagram of an example connector including a plug and a socket, where the cross-section is taken through a central longitudinal axis of the connector.
Figure 3:
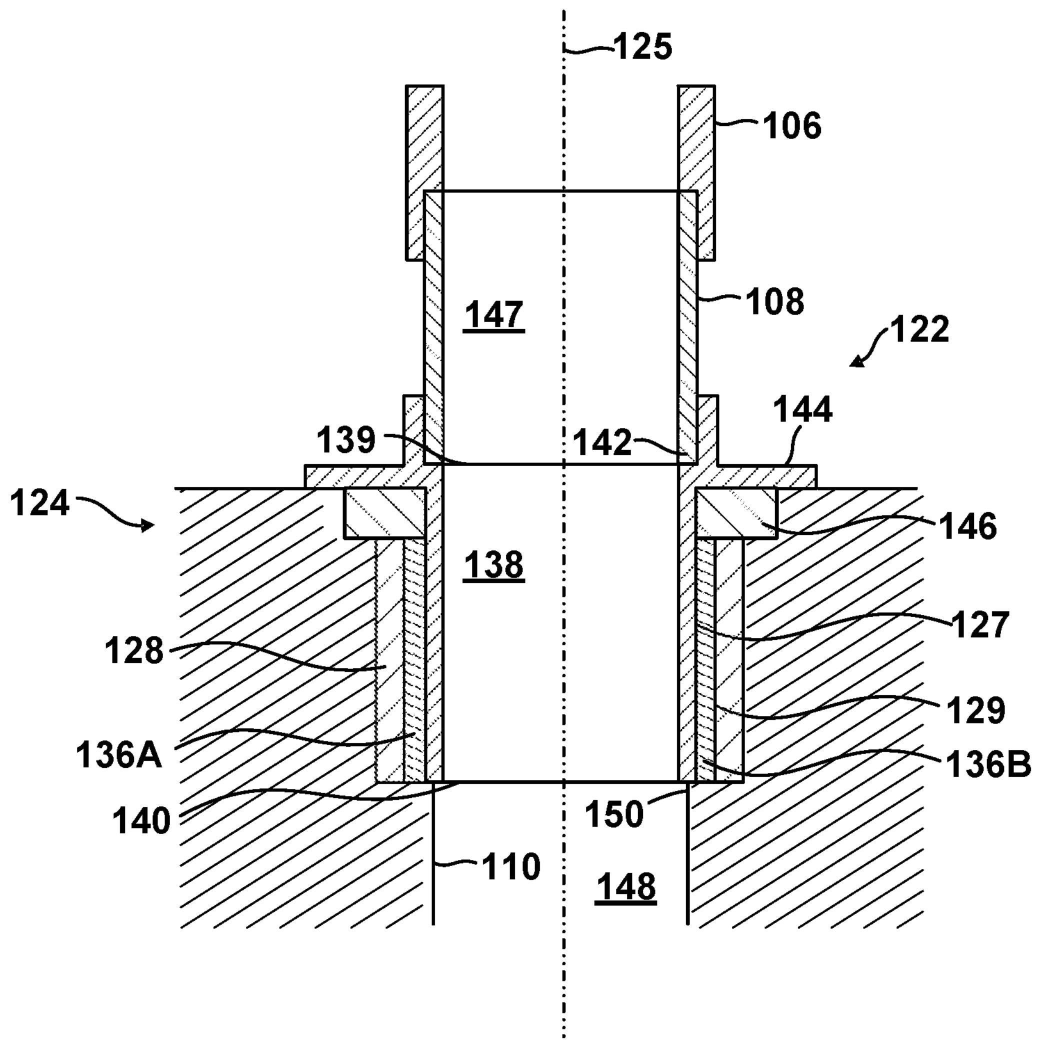
FIG. 3 is a conceptual cross-sectional diagram of the connector of FIG. 2 with the plug mechanically mated with the socket.

FIGS. 2 and 3 are conceptual cross-sectional diagrams of an example connector 102 including plug 122 including a plug body 126. The cross-section is taken along a central longitudinal axis 125 of connector 102. Connector 102 further includes socket 124 including a socket body 128. Plug 122 is configured to mechanically and fluidically engage first conduit 108 (e.g., a bag tube from a container 106) and socket 124 is configured to mechanically and fluidically engage second conduit 110 (e.g., a machine line). As shown in FIGS. 2 and 3, socket body 128 defines a socket well 134.

Plug 122 is configured to mechanically mate with socket 124 such that the first conduit 108 and the second conduit 110 are fluidically coupled. Plug body 126 defines a plug channel 138, which extends from a plug inlet 139 to a plug outlet 140. Plug inlet 139 and plug outlet 140 are openings defined by plug body 126. Plug channel 138 is configured to establish fluid communication between plug inlet 139 and plug outlet 140. Plug 122 is configured to mechanically and fluidically engage first conduit 108 in any manner sufficient to fluidly couple first conduit 108 and plug outlet 140. In some examples, plug 122 is configured to mechanically and fluidically engage first conduit 108 such that plug 122 establishes a substantially confined (e.g., confined but for manufacturing tolerances) flow path from a first flow channel 147 defined by first conduit 108 to plug inlet 139. Plug inlet 139 may be configured to receive first conduit 108 (e.g., a flexible or rigid tube). In some examples, plug inlet 139 may be configured to allow an end 142 of first conduit 108 ("first conduit end 142") to insert into plug channel 138 through plug inlet 139 in order to fluidly couple first conduit 108 and plug outlet 140. For example, FIGS. 2 and 3 illustrate first conduit 108 inserted through plug inlet 139, such that first conduit end 142 is positioned within plug channel 138 of plug 122.

Connector 102 includes a socket membrane 130 positioned within socket well 134. As shown in FIG. 2, socket membrane 130 is biased to a closed position in which socket membrane 130 fully or nearly fully seals socket 124, thereby substantially blocking the flow of material through socket well 134. Socket membrane 130 is configured to open in response to insertion of plug 122 into socket well 134. FIG. 3 illustrates an example in which socket membrane 130 is in an open position, e.g., is pushed open by plug 122 and positioned between an outer surface of plug 122 and an inner surface of socket well 134. Socket membrane 130 may advantageously also act as a fluid seal (e.g., similar to an O-ring) to help prevent fluids from leaking from between plug 122 and socket 124. Socket membrane 130 may be further configured to assume the closed position in response to removal of plug 122 from socket well 134.

Socket membrane 130 may have any suitable configuration that enables it to be biased to a closed position (FIG. 2) and open (FIG. 3) in response to a pushing force applied by plug 122. In some examples, socket membrane 130 is formed from a substantially non-compliant material attached to an elastic component (e.g., a spring) configured to resist displacement (e.g., in the first direction D1) of socket membrane 130 from the closed position. Additionally or alternatively, socket membrane 130 may be formed from a material with properties that enable socket membrane 130 to deform in response to force (e.g., in the first direction D1) imparted on socket membrane 130, and that enable socket membrane 130 to return to the closed position when the force is removed. For example, socket membrane 130 may be formed from a compliant material (e.g., a polymer) having an elasticity that enables at least a portion of socket membrane 130 to deform in response to force imparted by plug 122 on socket membrane 130 to define an opening sized to enable plug 122 to be inserted into socket well 134. Responsive to the removal of the force on socket membrane 130 (e.g., due to the removal of plug 122 from socket 124), the elasticity of socket membrane 130 may cause socket membrane 130 to return to the closed position. In some examples, socket membrane 130 may return to the closed position due to the application of a physical stimulus to socket membrane 130, such as heating socket membrane 130, sending an electric current through socket membrane 130, and/or the like. Thus, in some examples, socket membrane 130 may be formed from one or more of elastic polymer, shape memory material (e.g., a metal or polymer), harmonic steel, and/or the like. In other examples, socket membrane 130 is configured to return to the closed position without the application of an external stimulus, e.g., due to the shape memory properties of the material forming socket membrane 130, due the material properties or the use of a spring that biases socket membrane 130 to a closed position, or any other suitable technique.

Figures 4A, 4B:
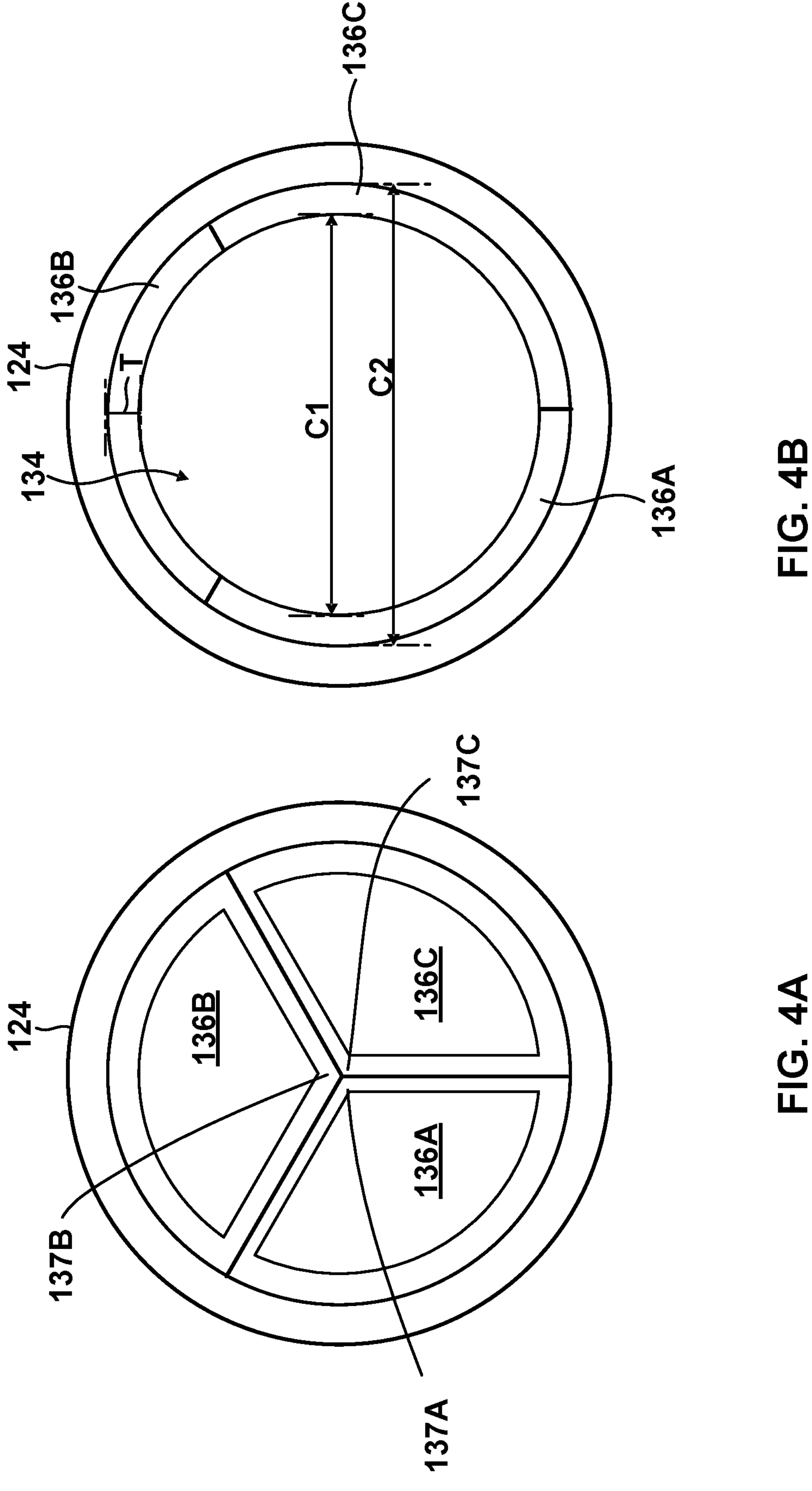
FIG. 4A is a conceptual plan diagram of the socket of FIG. 2 when a socket membrane of the socket is in a closed position.
FIG. 4B is a conceptual plan diagram of the socket of FIG. 2 when the socket membrane is in an open position.

In some examples, socket membrane 130 includes a plurality of leaflets 136A, 136B, 136C (collectively, "leaflets 136") configured to coapt to define the closed position. Leaflet 136C is shown in FIGS. 4A and 4B. Although three leaflets 136 are shown in FIGS. 2-4B, in other examples, socket membrane 130 can include any suitable number of leaflets, including two, four, five, or more leaflets. Leaflets 136 each defines a free edge configured to move distally away (i.e., in a first direction D1) from plug inlet 139 when plug 122 is inserted into socket well 134 to open socket membrane 130. When socket membrane 130 is opened, socket membrane 130 is configured to enable fluid through plug flow through socket well 134 past socket membrane 130, e.g., from a location on one side of socket membrane 130 to a location on another side of socket membrane 130.

Leaflets 136 may be configured to position between an outer surface 127 of plug 122 ("plug outer surface 127") and an inner surface 129 of socket well 134 ("socket well inner surface 129") defining socket well 134 in response to insertion of plug 122 into socket well 134. For example, leaflets 136 may be elastic such that at least a portion of socket membrane 130 deforms in response to force imparted by plug 122 on leaflets 136 to define an opening sized to enable plug 122 to be inserted into socket well 134. For similar reasons and in a similar fashion, leaflets 136 may be further configured to undeform and assume the closed position in response to removal of plug 122 from socket well 134.

FIG. 3 illustrates plug 122 inserted in socket well 134 and mechanically mated with socket 124. Socket 124 may be configured to mechanically mate with plug 122 when plug 122 is translated in a first direction D1 toward socket 124. In some examples, one of plug 122 or socket 124 defines a protrusion and the other of plug 122 or socket 124 defines a recess, and the recess is configured to receive the protrusion when socket 124 mechanically mates with plug 122. Plug 122 and socket 124 may be configured such that the mechanical mating limits movement of plug 122 relative to socket 124 at least in a direction substantially perpendicular to the first direction D1. In some examples, one or more surfaces of socket 124 may be configured to substantially conform to one or more surfaces of plug 122 when socket 124 mechanically mates with plug 122. For example, plug outer surface 127 may define a complementary shape to a shape of socket well inner surface 129, such that plug outer surface 127 and socket well inner surface 129 limits movement of plug 122 relative to socket 124 at least in a direction substantially perpendicular to the first direction D1. In examples, plug outer surface 127 may be configured to contact socket well inner surface 129 when socket 124 mechanically mates with plug 122. As described above, leaflets 136 may be configured to position between plug outer surface 127 and the socket well inner surface 129 in response to insertion of plug 122 into socket well 134.

In some examples, plug 122 and socket 124 may be configured such that the mechanical mating limits movement of plug 122 relative to socket 124 at least in a direction substantially parallel to the first direction D1. For example, a rim 144 may extend from plug body 126, e.g., from plug outer surface 127, where rim 144 is configured to contact socket body 128 to control a depth of insertion of plug 122 into socket well 134. In some examples, socket body 128 or housing 105 of machine 104 may include a flange 146 configured to provide structural support for socket membrane 130. Flange 146 may be further configured to contact rim 144 when plug 122 is fully inserted into socket well 134. In some examples, flange 146 may extend radially outward from a portion of socket body 128 defining socket well 134 or may be flush with the rest of the outer surface of socket body 128. Similarly, in some examples, flange 146 may extend radially outward from a portion of housing 105 or may be flush with the rest of the outer surface of housing. In some examples, rim 144 and flange 146 may include one or more visual indicia (e.g., colors, graphical markers, or text) that help a user align plug 122 with the proper socket 124.

In an example, plug body 126 defines a protrusion configured to insert into socket well 134 defined by socket body 128 to mechanically mate plug 122 and socket 124. In examples, plug body 126 is configured to establish a sliding contact with socket membrane 130 when plug 122 is inserted into socket well 134. For example, plug outer surface 127 may define an outer periphery (e.g., a circumference) of plug 122, and leaflets 136, when positioned between plug outer surface 127 and socket well inner surface 129, may define an inner periphery of socket 124. In this example, leaflets 136 may be configured to establish a sliding contact with plug outer surface 127 around substantially the entirety of the outer periphery and the inner periphery.

Socket 124 is configured to mechanically and fluidically engage second conduit 110. Second conduit 110 may be, for example, a machine line of medical machine 104. In examples, socket 124 is configured to mechanically and fluidically engage second conduit 110 such that, when plug 122 mechanically mates with socket 124, plug channel 138 fluidly couples with second conduit 110. Socket 124 may be configured such that the mechanical mating of plug 122 and socket 124 establishes a substantially confined flow path from plug channel 138 to a second flow channel 148 defined by second conduit 110. Hence, connector 102 may be configured to form a physical, fluid connection between first conduit 108 (e.g., tubing for a container 106 (FIG. 1)) and second conduit 110 (e.g., a machine line for medical machine 104 (FIG. 1)) when plug 122 mechanically mates with socket 124. In examples, housing 105 of medical machine 104 mechanically supports socket 124 and/or second conduit 110. In examples, socket 124 may be affixed to or an integral part of medical machine 104 and/or housing 105. Second conduit 110 may be affixed to or an integral part of socket 124, medical machine 104, and/or housing 105.

Socket 124 may be configured to mechanically and fluidically engage second conduit 110 in any manner sufficient to fluidly couple plug channel 138 with second conduit 110 when plug 122 mechanically mates with socket 124. For example, an end 150 of second conduit 110 ("second conduit end 150") may be configured to insert through plug outlet 140 and into plug channel 138 when plug 122 mechanically mates with socket 124. In examples, socket 124 is configured to mechanically and fluidically engage second conduit 110 such that plug 122 establishes a substantially confined flow path from plug channel 138 to second flow channel 148 of second conduit 110. Socket 124 may be configured to mechanically and fluidically engage second conduit 110 such that plug 122 establishes a substantially confined flow path from first flow channel 147 of first conduit 108 to second flow channel 148 of second conduit 110.

FIGS. 4A and 4B are conceptual plan diagrams of an example socket 124 including socket membrane 130. Longitudinal axis 125 runs orthogonal to the plane of the image of FIGS. 4A and 4B. In the example shown in FIGS. 4A and 4B, socket membrane 130 includes three leaflets 136A, 136B, and 136C configured to coapt to define a closed position of socket membrane 130. Leaflets 136 may also define respective free ends 137 configured to move distally away from plug 122 when plug 122 is inserted into socket well 134.

Leaflets 136 may be connected to socket body 128 using any suitable technique, such as, but not limited to, overmolding, co-molding, welding (e.g., ultrasonic welding), using an adhesive, mechanical attachment mechanisms (e.g., screws or the like), interlocking structures, and/or the like. For example, an end of each leaflet 136 opposite the respective free end 137 may be attached to socket well inner surface 129. In other examples, one or more leaflets 136 may be integrally formed with socket body 128, rather than separately formed from and connected thereto.

As shown in FIG. 4A, leaflets 136 of socket membrane 130 are biased to a closed position, in which leaflets 136 are coapted (e.g., each free end 137 is touching or otherwise relatively close to an adjacent free end), to block fluid flow through socket well 134. When in the closed position, leaflets 136 work together to fully or nearly fully seal (or, in other words, block) socket well 134, thereby substantially blocking the flow of material through socket well 134. In this way, leaflets 136 may work together to close the fluid path through socket well 134 when leaflets 136 are biased to the closed position.

As shown in FIG. 4B, leaflets 136 of socket membrane 130 are configured to open to enable fluid flow through socket well 134 in response to a force imparted on leaflets 136. In some examples, leaflets 136 are elastic such that at least a portion of leaflets 136 deforms in response to force imparted by plug 122 on leaflets 136 to define an opening sized to enable plug 122 to be inserted into socket well 134. Leaflets 136 may be configured to position between plug outer surface 127 and socket well inner surface 129 in response to insertion of plug 122 into socket well 134. Alternatively, leaflets 136 may be formed from a substantially non-compliant material and attached to an elastic component configured to resist displacement of leaflets 136 from the closed position. Responsive to removal of plug 122 from socket well 134, leaflets 136 may return to the closed position. In some examples, leaflets 136 may be formed from one or more of an elastic polymer, shape memory material, harmonic steel, and/or the like, and, in some examples, the application of an external stimulus to socket membrane 130, such as heat or electricity, may cause leaflets 136 to return to the closed position.

In some examples, plug 122 defines an outer cross-sectional dimension C1 (e.g., a diameter) and socket well 134 defines an inner cross-sectional dimension C2 (e.g., a diameter). Plug 122 may be configured such that outer dimension C1 enables plug 122 to insert into socket well 134 having inner dimension C2 when plug 122 mechanically mates with socket 124 and when socket membrane 130 with a thickness T is positioned between plug outer surface 127 and socket well inner surface 129. For example, plug 122 may be configured such that outer dimension C1 causes a plug 122 to establish a sliding fit with socket membrane 130 having thickness T when plug 122 mechanically mates with socket 124.

Figure 5:
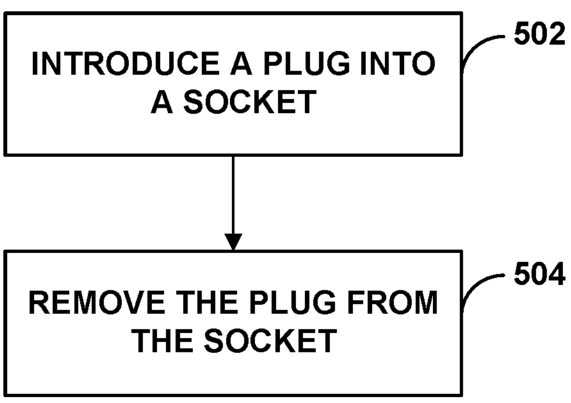
FIG. 5 is a flow diagram of an example technique of using a connector.

An example technique for connecting a container with medical machine 104 is illustrated in FIG. 5. Although the technique is described mainly with reference to connector 102 of FIGS. 1-4, the technique may be applied to other connectors and in other examples.

The technique includes introducing a plug 122 into socket 124 (502). Socket 124 may be configured to mechanically mate with plug 122 when plug 122 is translated in a first direction D1 toward socket 124. As discussed above, responsive to insertion of plug 122 into socket 124, socket membrane 130 opens to enable fluid flow through socket well 134 to establish a confined fluid path extending from the interior of a container (e.g., container 106), through connector 102, and to flow path 118. For example, leaflets 136 of socket membrane 130 may define free edges configured to move distally away from plug 122 when plug 122 is inserted into socket well 134. Leaflets 136 may be configured to position between plug outer surface 127 and socket well inner surface 129 in response to insertion of plug 122 into socket well 134. In some examples, leaflets 136 may be elastic such that at least a portion of leaflets 136 deforms in response to force imparted by plug 122 on leaflets 136 to define an opening sized to enable plug 122 to be inserted into socket well 134.

The technique includes removing plug 122 from socket 124 (504). Responsive to the removal of a force being imparted on socket membrane 130, socket membrane 130 may return to the closed position in which socket membrane 130 fully or nearly fully seals socket 124, thereby substantially blocking the flow of material through socket well 134. For example, leaflets 136 may be configured to coapt to define the closed position. In some examples, the integration of socket membrane 130 into socket 124 may make it unnecessary to reposition socket membrane 130 after removal of plug 122, thereby helping ensure the sterility of the medical machine.

The present disclosure includes the following examples.

Example 1: A connector includes a plug defining a channel extending between a plug inlet defined by the plug and a plug outlet defined by the plug, wherein the plug inlet is configured to mechanically and fluidically engage a first conduit; a socket includes a socket body defining a socket well, wherein the socket is configured to mechanically and fluidically engage a second conduit, and wherein the plug is configured to insert into the socket well to mechanically mate with the socket; and a socket membrane biased to a closed position in which the socket membrane blocks fluid flow through the socket well, and wherein, when the plug is inserted into the socket well, the socket membrane is configured to open to enable fluid flow through the socket well.

Example 2: The connector of example 1, wherein the socket membrane is positioned within the socket well.

Example 3: The connector of example 1 or example 2, further comprising a dialysis machine housing, wherein the socket membrane is connected to the dialysis machine housing.

Example 4: The connector of any of examples 1-3, wherein the socket membrane is deformable and configured to position between an outer surface of the plug and an inner surface of the socket well in response to insertion of the plug into the socket well.

Example 5: The connector of example 4, wherein the socket membrane is further configured to undeform and assume the closed position in response to one or more of a removal of the plug from the socket well or an application of a physical stimulus to the socket membrane.

Example 6: The connector of any of examples 1-5, wherein the socket membrane comprises at least two leaflets configured to coapt to define the closed position.

Example 7: The connector of example 6, wherein the leaflets define free edges configured to move distally away from the plug when the plug is inserted into the socket well.

Example 8: The connector of any of examples 1-7, wherein the socket is configured to fluidly couple the plug inlet and the second conduit when the plug mechanically mates with the socket and the socket mechanically and fluidically engages the second conduit.

Example 9: The connector of any of examples 1-8, wherein the plug further comprises a rim extending from an outer surface of the plug, and wherein the rim is configured to contact the socket body to control a depth of insertion of the plug into the socket well.

Example 10: The connector of example 9, wherein one of the socket body or a housing of a dialysis machine comprises a flange configured to contact the rim when the plug is fully inserted in the socket well.

Example 11: The connector of any of examples 1-10, wherein the plug and the socket comprise respective visible indications to indicate that the plug is configured to mechanically mate with the socket body.

Example 12: The connector of any of examples 1-11, wherein the socket membrane is formed using one or more of an elastic polymer, a shape memory material, or harmonic steel.

Example 13: A medical system includes a plug defining a channel extending between a plug inlet defined by the plug and a plug outlet defined by the plug, wherein the plug inlet is configured to mechanically and fluidically engage a tubing; a dialysis machine includes a socket body defining a socket well, wherein the plug is configured to insert into the socket well to mechanically mate with the socket and to fluidically connect the plug inlet and the hydraulic line; and a socket membrane positioned within the socket well, wherein the socket membrane is biased to a closed position in which the socket membrane blocks fluid flow through the socket well, and wherein, when the plug is inserted into the socket well, the socket membrane is configured to open to enable fluid flow through the socket well.

Example 14: The medical system of example 13, wherein the socket membrane is deformable and configured to position between an outer surface of the plug and an inner surface of the socket well in response to insertion of the plug into the socket well.

Example 15: The medical system of example 14, wherein the socket membrane is further configured to undeform and assume the closed position in response to one or more of a removal of the plug from the socket well or an application of a physical stimulus to the socket membrane.

Example 16: The medical system of any of examples 13-15, wherein the socket membrane comprises at least two leaflets configured to coapt to define the closed position.

Example 17: The medical system of example 16, wherein the leaflets define free edges configured to move distally away from the plug when the plug is inserted into the socket well.

Example 18: The medical system of any of examples 13-17, wherein the socket is configured to fluidically couple the plug inlet and the hydraulic line when the plug mechanically mates with the socket and the socket mechanically and fluidically engages the hydraulic line, and wherein the hydraulic line is in fluid communication with a dialysis cycler.

Example 19: The medical system of any of examples 13-18, further comprising the tubing, wherein the tubing is configured to fluidically connect to a container including a dialysate component.

Example 20: A method comprising inserting a plug of any of claims 1-19 into a socket well defined by a socket of any of claims 1-19 and subsequently removing the plug from the socket.

Various examples of the disclosure have been described. Any combination of the described systems, operations, or functions is contemplated. These and other examples are within the scope of the following claims.

What is claimed is:

1. A medical system comprising:

a plug defining a channel extending between a plug inlet defined by the plug and a plug outlet defined by the plug, wherein the plug inlet is configured to mechanically and fluidically engage a tubing;

a dialysis machine comprising a hydraulic line and a socket fluidically connected to an end of the hydraulic line, wherein the socket comprises:

a socket body including a flange and including a socket well inner surface, wherein the socket well inner surface defines a socket well, wherein the flange defines an opening which opens into the socket well, wherein the hydraulic line is mechanically engaged with the socket body, and wherein the plug is configured to insert through the opening of the flange and into the socket well to mechanically mate with the socket and to fluidically connect the plug inlet and an outlet defined by the end of the hydraulic line; and a socket membrane supported by the socket well inner surface between the flange and the end of the hydraulic line, wherein the socket membrane comprises at least three substantially equal-section leaflets including a first leaflet, a second leaflet, and a third leaflet and the at least three leaflets are biased to a closed position in which the socket membrane block a fluid flow through the socket well, and wherein the first leaflet comprises a first free end, the second leaflet comprises a second free end, and the third leaflet comprises a third free end and, when the plug is inserted into the socket well, the first free end, the second free end, and the third free end are configured to move distally away from the plug and transition to an open position to enable the fluid flow through the socket well, wherein the plug further comprises an outer surface defining a first portion and a rim portion, the rim portion extending more radially outwards than the first portion and configured to contact the flange, wherein the plug is configured to insert into the socket well in a first direction extending from the flange toward the end of the hydraulic line, wherein the plug is configured to linearly translate against the socket membrane in the first direction until the rim portion contacts the flange, and wherein the first portion is configured to remain outside of the socket well when the plug is inserted into the socket well.

2. The medical system of claim 1, wherein the hydraulic line is supported by the dialysis machine, and wherein the socket body is affixed to a housing of the dialysis machine.

3. The medical system of claim 1, wherein the plug and the socket comprise respective visible indications to indicate that the plug is configured to mechanically mate with the socket body.

4. The medical system of claim 1, wherein the socket membrane is deformable and configured to position between the plug and the socket well inner surface in response to insertion of the plug into the socket well.

5. The medical system of claim 4, wherein the socket membrane is further configured to undeform and assume the closed position in response to one or more of a removal of the plug from the socket well or an application of a physical stimulus to the socket membrane.

6. The medical system of claim 1, wherein the first leaflet, the second leaflet, and the third leaflet are biased to coapt to define the closed position.

7. The medical system of claim 1, wherein the socket is configured to fluidically couple the plug inlet and the outlet of the hydraulic line when the plug mechanically mates with the socket and the socket mechanically and fluidically engages the hydraulic line, wherein the outlet of the hydraulic line is defined by the end of the hydraulic line.

8. The medical system of claim 1, further comprising the tubing, wherein the plug inlet is mechanically and fluidically engaged to the tubing, and wherein the tubing is fluidically connected to a container configured to hold a dialysate component.

9. The medical system of claim 6, wherein the first leaflet includes a first supported end supported by a portion of the socket well inner surface between the flange and the end of the hydraulic line and the first free end opposite the first supported end, wherein the first free end is configured to move distally away from the plug when the plug is inserted into the socket well and the socket membrane transitions to the open position, and wherein the second leaflet includes a second supported end supported by the portion of the socket well inner surface between the flange and the end of the hydraulic line and the second free end opposite the first supported end, and wherein the second free end is configured to move distally away from the plug when the plug is inserted into the socket well and the socket membrane transitions to the open position.

10. The medical system of claim 9, wherein the first free end of the first leaflet is configured to contact the second free end of the second leaflet when the socket membrane is biased to the closed position.

11. The system of claim 1, wherein, in the closed position, the first free end, the second free end, and the third free end touch at a meeting point along a central longitudinal axis of the socket body, wherein the at least three substantially equal-section leaflets comprise a substantially equal section of a circle.

12. The system of claim 1, wherein the flange comprises a first surface facing an exterior environment, a second surface connected and orthogonal to the first surface, and a third surface facing the socket well and connected to the second surface, wherein the second surface defines the opening, and wherein the plug slides along the second surface when the plug is inserted into the socket well in the first direction.

13. The system of claim 1, wherein an entirety of the socket membrane is recessed along the first direction with respect to the opening when the socket membrane is in the closed position and when the socket membrane is in the open position.

14. A medical system comprising:

a plug defining a channel extending between a plug inlet defined by the plug and a plug outlet defined by the plug, wherein the plug inlet is configured to mechanically and fluidically engage a first conduit, and wherein the plug further comprises an outer surface defining a first portion and a rim portion, the rim portion extending more radially outwards than the first portion;

a dialysis machine comprising a second conduit and a socket fluidically connected to an end of the second conduit, the socket comprising:

a socket body including a flange and including a socket well inner surface, wherein the socket well inner surface defines a socket well, wherein the flange defines an opening which opens into the socket well, wherein the second conduit is mechanically engaged with the socket body, wherein the plug is configured to insert through the opening of the flange and into the socket well to mechanically mate with the socket and fluidically connect the plug inlet and an outlet defined by the end of the second conduit, wherein the rim portion is configured to contact the flange when the plug mechanically mates with the socket, and wherein a housing of the dialysis machine mechanically supports the socket body; and a socket membrane supported by the socket well inner surface between the flange and the end of the second conduit, wherein the socket membrane comprises at least three substantially equal-section leaflets including a first leaflet, a second leaflet, and a third leaflet and the at least three leaflets are biased to a closed position in which the socket membrane blocks a fluid flow through the socket well, and wherein the first leaflet comprises a first free end, the second leaflet comprises a second free end, and the third leaflet comprises a third free end, and, when the plug is inserted into the socket well, the first free end, the second free end, and the third free end are configured to move distally away from the plug to transition to an open position to enable the fluid flow through the socket well, wherein the plug is configured to insert into the socket well in a first direction extending from the flange to the end of the second conduit, wherein the plug is configured to linearly translate against the socket membrane in the first direction until the rim portion contacts the flange, and wherein the first portion is configured to remain outside of the socket well when the plug is inserted into the socket well.

15. The medical system of claim 14, wherein the socket membrane is positioned within the socket well.

16. The medical system of claim 14, wherein the socket membrane is deformable and configured to position between the outer surface of the plug and the socket well inner surface in response to insertion of the plug into the socket well.

17. The medical system of claim 16, wherein the socket membrane is further configured to undeform and assume the closed position in response to one or more of a removal of the plug from the socket well or an application of a physical stimulus to the socket membrane.

18. The medical system of claim 14, wherein the first, second and third leaflets are biased to coapt to define the closed position.

19. The medical system of claim 14, wherein the second conduit is supported by the dialysis machine, and wherein the socket body is affixed to the housing of the dialysis machine.

20. A method comprising:

inserting a plug through a socket membrane and into a socket well defined by a socket, wherein:

the plug defines a channel extending between a plug inlet defined by the plug and a plug outlet defined by the plug, wherein the plug inlet is configured to mechanically and fluidically engage a first conduit, the socket comprises a socket body including a flange and including a socket well inner surface, wherein the socket well inner surface defines the socket well, wherein the flange defines an opening which opens into the socket well, wherein the socket well is fluidically connected to an end of a second conduit of a medical machine, wherein the second conduit is mechanically engaged with the socket body, and wherein the plug is configured to insert into the socket well to mechanically mate with the socket and to fluidically connect the plug inlet and the second conduit, the socket membrane is supported by the socket well inner surface between the flange and the end of the second conduit, wherein the socket membrane comprises at least three substantially equal-section leaflets including a first leaflet, a second leaflet, and a third leaflet and the at least three leaflets are biased to a closed position in which the socket membrane blocks a fluid flow through the socket well, and wherein inserting the plug into the socket well opens the socket membrane to enable the fluid flow through the socket well from the plug inlet to the second conduit, the plug further comprises an outer surface defining a first portion and a rim portion, the rim portion extending more radially outwards than the first portion and configured to contact the flange, the plug is configured to insert into the socket well in a first direction from the flange to an outlet of the second conduit, and the plug is configured to linearly translate against the socket membrane in the first direction until the rim portion contacts the flange, and the first portion is configured to remain outside of the socket well when the plug is inserted into the socket well; and, subsequently, removing the plug from the socket.

21. The method of claim 20, wherein the second conduit is supported by a dialysis machine, and wherein the socket body is affixed to a housing of the dialysis machine.

* * * * *